US 8,570,208 B2

(12) United States Patent
Sarkis

(10) Patent No.: US 8,570,208 B2
(45) Date of Patent: Oct. 29, 2013

(54) RADAR TOMOGRAPHY APPARATUS AND METHOD

(75) Inventor: Michel Sarkis, Stuttgart (DE)

(73) Assignee: Sony Corporation, Tokyo (JP)

( * ) Notice: Subject to any disclaimer, the term of this patent is extended or adjusted under 35 U.S.C. 154(b) by 202 days.

(21) Appl. No.: 13/177,952

(22) Filed: Jul. 7, 2011

(65) Prior Publication Data

US 2012/0019406 A1   Jan. 26, 2012

(30) Foreign Application Priority Data

Jul. 16, 2010   (EP) .................................... 10169816

(51) Int. Cl.
 *G01S 13/89* (2006.01)
(52) U.S. Cl.
 USPC .............. 342/22; 342/179; 342/180; 342/196
(58) Field of Classification Search
 USPC ............ 342/22, 179–180, 191, 192, 194–196
 See application file for complete search history.

(56) References Cited

U.S. PATENT DOCUMENTS

| | | | | |
|---|---|---|---|---|
| 6,697,660 | B1* | 2/2004 | Robinson ...................... | 600/409 |
| 7,570,742 | B2* | 8/2009 | Johnson et al. ............... | 600/309 |
| 7,684,846 | B2* | 3/2010 | Johnson et al. ............... | 600/407 |
| 7,755,010 | B2* | 7/2010 | Godshalk et al. ............. | 219/679 |
| 2006/0084859 | A1* | 4/2006 | Johnson et al. ............... | 600/407 |
| 2006/0257010 | A1 | 11/2006 | George et al. | |
| 2008/0140341 | A1* | 6/2008 | Ralston et al. ................ | 702/155 |
| 2009/0136089 | A1 | 5/2009 | Singh | |
| 2010/0001901 | A1 | 1/2010 | Baraniuk et al. | |
| 2011/0181461 | A1* | 7/2011 | Sarkis ........................... | 342/179 |
| 2011/0241934 | A1* | 10/2011 | Sarkis ........................... | 342/191 |
| 2012/0019406 | A1* | 1/2012 | Sarkis ........................... | 342/22 |
| 2012/0062408 | A1* | 3/2012 | Bausov et al. .................. | 342/22 |
| 2012/0163727 | A1* | 6/2012 | Jeon et al. ..................... | 382/254 |
| 2012/0188118 | A1* | 7/2012 | Sarkis ........................... | 342/179 |
| 2012/0194823 | A1* | 8/2012 | Moore et al. .................. | 356/479 |

OTHER PUBLICATIONS

Smolik, W.T.; Radomski, D., "An application of a regular square mesh in a forward problem solver in electrical capacitance tomography," Imaging Systems and Techniques (IST), 2011 IEEE International Conference on , vol., No., pp. 104,107, May 17-18, 2011.*

Crocco, L.; Prisco, G.; Soldovieri, F.; Cassidy, N.J., "Advanced forward modeling and tomographic inversion for leaking water pipes monitoring," Advanced Ground Penetrating Radar, 2007 4th International Workshop on , vol., No., pp. 127,131, Jun. 27-29, 2007.*

(Continued)

*Primary Examiner* — John B Sotomayor
(74) *Attorney, Agent, or Firm* — Oblon, Spivak, McClelland, Maier & Neustadt, L.L.P.

(57) ABSTRACT

A radar tomography apparatus and method determines one or more material properties of an object at a first number of positions distributed within a region of interest of said object. The apparatus includes one or more transmitters that transmit radiation, in particular microwave radiation, in the direction of the region of interest of the object, a plurality of receivers that receive radiation reflected from or transmitted through the region of interest of the object, a processor that processes the received radiation, said processor including a forward solver that determines electromagnetic field values at a second number of positions distributed in the region of interest from the received radiation.

13 Claims, 5 Drawing Sheets

(56) References Cited

OTHER PUBLICATIONS

Jun Cui, Tie; Weng Cho Chew; Yunhua Zhang, "Detection of dielectric targets buried in a very lossy Earth," Antennas and Propagation Society International Symposium, 2002. IEEE, vol. 2, No., pp. 769,772 vol. 2, 2002.*

Soleimani, M.; Lionheart, W.R.B., "Absolute Conductivity Reconstruction in Magnetic Induction Tomography Using a Nonlinear Method," Medical Imaging, IEEE Transactions on, vol. 25, No. 12, pp. 1521,1530, Dec. 2006.*

A. E. Bulyshev, et al. "Three-Dimensional vector microwave tomography: theory and computational experiments", Inverse Problems, Institute of Physics Publishing, Aug. 2004, 21 pages.

Zhong Qing Zhang, et al. "Three-Dimensional Nonlinear Image Reconstruction for Microwave Biomedical Imaging", IEEE Transactions on Biomedical Engineering, vol. 51, No. 3, Mar. 2004, 5 pages.

David W. Winters, et al. "Three-Dimensional Microwave Breast Imaging: Dispersive Dielectric Properties Estimation Using Patient-Specific Basis Functions", IEEE Transactions on Medical Imaging, vol. 28, No. 7, Jul. 2009, 13 pages.

Qianqian Fang, et al. "Microwave Image Reconstruction From 3-D Fields Coupled to 2-D Parameter Estimation", IEEE Transactions on Medical Imaging, vol. 23, No. 4, Apr. 2004, 10 pages.

Emmanuel Candes, et al. "Robust Uncertainty Principles: Exact Signal Reconstruction from Highly Incomplete Frequency Information", IEEE Transactions on Information Theory, Feb. 2006, 41 pages.

Hengyong Yu, et al. "Compressed sensing based interior tomography", Physics in Medicine and Biology, IOP Publishing, Apr. 2009, 15 pages.

David L. Donoho, "Compressed Sensing", IEEE Transactions on Information Theory, Sep. 14, 2004, 34 pages.

Richard Baraniuk, et al. "Compressive Radar Imaging", IEEE Radar Conference, Apr. 2007, 6 pages.

Mathew A. Herman, et al. "High-Resolution Radar via Compressed Sensing", IEEE Transactions on Signal Processing, 2008, 10 pages.

\* cited by examiner

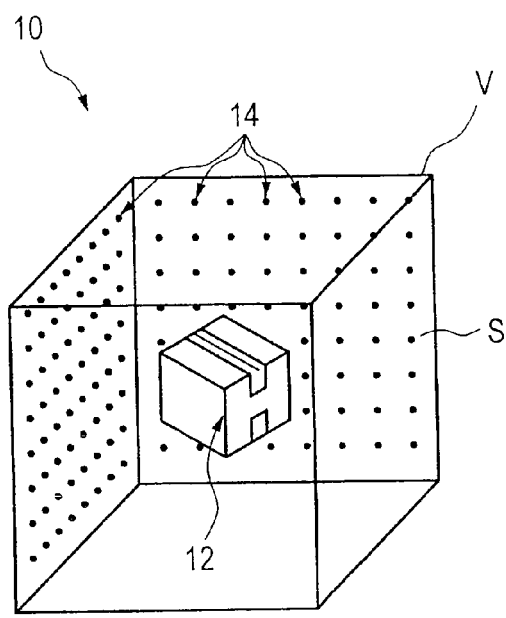
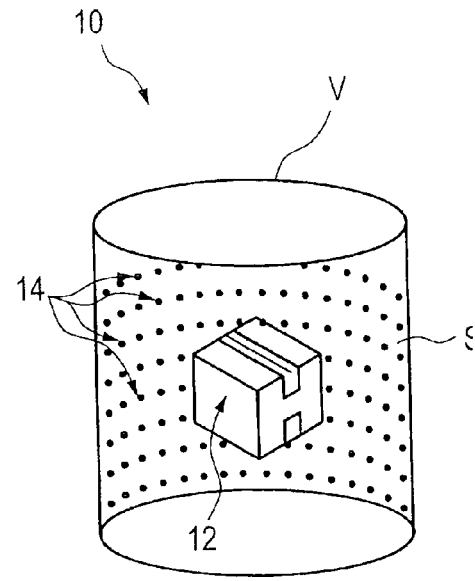
Fig. 1A
Fig. 1B
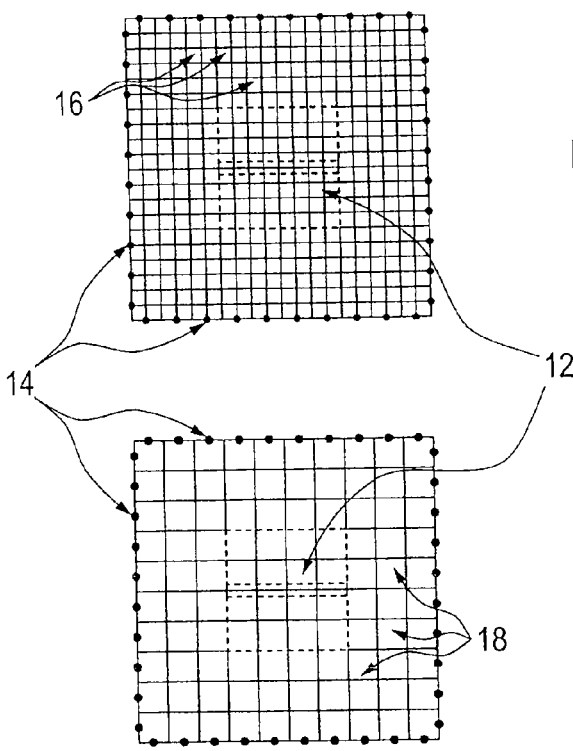
Fig. 2A
Fig. 2B

RADAR TOMOGRAPHY APPARATUS AND METHOD

CROSS-REFERENCE TO RELATED APPLICATIONS

The present application claims priority of European patent application 10 169 816.5 filed on Jul. 16, 2010.

FIELD OF THE INVENTION

The present invention relates to a radar tomography apparatus and a corresponding method for determining one or more material properties of an object at a first number of positions distributed within a region of interest of said object. Further, the present invention relates to a computer program for implementing said method and a computer-readable non-transitory medium.

BACKGROUND OF THE INVENTION

The invention relates to radar tomography, according to which unknown material properties, in particular electromagnetic properties, of an object shall be measured. The concept of radar tomography is generally known, for instance from A. E. Bulyshev et al. "Three-dimensional vector microwave tomography: theory and computational experiments", Inverse Problems, August 2004, Z. Q. Zhang et Q. H. Liu. "Three-Dimensional Nonlinear Image Reconstruction for Microwave Biomedical Imaging", IEEE Transactions on Biomedical Engineering, March 2004, D. W. Winters et al., "Three-Dimensional Microwave Breast Imaging: Dispersive Dielectric Properties Estimation Using Patient-Specific Basis Functions", IEEE Transactions on Medical Imaging, July 2009, and Q. Fang et al., "Microwave Image Reconstruction From 3-D Fields Coupled to 2-D Parameter Estimation", IEEE Transactions on Medical Imaging, April 2004.

The object, e.g. a patient or tissue material, is placed in an area surrounded by antenna elements (generally, by transmitters). The area can have the form of a cuboid or a cylinder for example. The region of interest of the object, in which the material properties shall be determined, is divided into a mesh. The actual tomography includes two main elements. The first element is a forward solver in which the complex electromagnetic fields at all the elements of the mesh are determined. The second element is an inverse solver in which the unknown material properties of the object are computed from the complex electromagnetic fields. Each of these processes is done once or repeated sequentially several times until the desired accuracy of the results is achieved.

The complexity of a radar tomography device mainly depends on the density of the mesh (number of elements or regions in the mesh, e.g. pixels or voxels), the operating dimensions (1D, 2D or 3D) and the number of transmitters and receivers (or transceivers). Considering for example a cubic region of dimensions $15 \times 15 \times 15$ cm$^3$ and dividing it into $100 \times 100 \times 100$ voxels or 1 million elements, determining the 3D components of the complex field at all the voxels requires resolving for $3 \times 1$ million or 3 million variables. If the complex electromagnetic field is approximated by a scalar, as done in many state of the art algorithms, the number of variables drops back to 1 million. These numbers have to be resolved in both the forward and backward solvers for each transmitted signal. Hence, the complexity of the problem increases dramatically with the increase in the mesh density and the number of transceivers used.

To limit the complexity in radar tomography, an obvious solution is trying to reduce the density of the mesh by having larger mesh elements (i.e. a more coarse grid). However, this solution also reduces the quality of the obtained result (e.g. of an image reconstructed from the determined material properties). Another obvious solution is trying to limit the meshed area to the object or the region of interest, but this solution still has high complexity, especially in 3D, unless the dimension of the mesh elements (i.e. voxel size) is also large.

BRIEF SUMMARY OF THE INVENTION

It is an object of the present invention to provide a radar tomography device and method, by which both the process of radar tomography, i.e. the acquisition of data, can be accelerated and the computational demand for evaluating and processing the acquired data can be reduced. It is a further object of the present invention to provide a corresponding computer program for implementing said method and a computer readable non-transitory medium.

According to an aspect of the present invention there is provided a radar tomography apparatus for determining one or more material properties of an object at a first number of positions distributed within a region of interest of said object, said apparatus comprising:
one or more transmitters that transmit radiation, in particular microwave radiation, in the direction of the region of interest of the object,
a plurality of receivers that receive radiation reflected from or transmitted through the region of interest of the object,
a processor that processes the received radiation, said processor including
a forward solver that determines electromagnetic field values at a second number of positions distributed in the region of interest from the received radiation, wherein said second number is substantially lower than said first number, and
an inverse solver that determines one or more material properties of the object at the first number of positions in the region of interest from the electromagnetic field values determined at said second number of positions in the region of interest by applying compressive sensing.

According to a further aspect of the present invention there is provided a corresponding radar tomography method.

According to still further aspects a computer program comprising program means for causing a computer to carry out the steps of the method according to the present invention, when said computer program is carried out on a computer, as well as a computer readable non-transitory medium having instructions stored thereon which, when carried out on a computer, cause the computer to perform the steps of the method according to the present invention are provided.

Preferred embodiments of the invention are defined in the dependent claims. It shall be understood that the claimed method, the claimed computer program and the claimed computer readable medium have similar and/or identical preferred embodiments as the claimed device and as defined in the dependent claims.

The present invention is based on the idea to apply compressed (also called compressive) sensing. Compressed or compressive sensing (CS) is the art of reconstructing a signal from some distributed, e.g. random, pseudo-random or irregular, measurements (here the electromagnetic field values) that directly condense the original signal into a compressed representation. The measurements acquired are condensed in the sense that they are (very) low in number, which makes further compression not necessary. CS differs from the traditional data acquisition schemes since it does not follow the "sample first—then compress" framework. However, to reconstruct, for instance, an image from the (reduced number of) measurement, the original signal needs to be reconstructed first from said (reduced number of) measurements.

Applying compressive sensing according to the present invention, the region of interest of the object, where the material (electromagnetic) properties shall be computed, is divided into a mesh as usually done in radar tomography. However, the forward solver is then invoked to compute the electromagnetic fields on some predefined parts of the mesh which will lead to an electromagnetic field at the selected mesh elements only, i.e. at a second (low) number of positions. Hereinafter, this electromagnetic field will also be called the sparse electromagnetic field. The inverse solver then uses the sparse computed electromagnetic fields to determine the material properties at a plurality of or all the elements of the mesh, i.e. at the first (high) number of positions, said first number being substantially higher than said second number.

To integrate compressive sensing in the acquisition process of radar tomography, the electromagnetic field values are determined only at a plurality of (preferably equally) distributed positions across the region of interest (i.e. the mesh), resulting in a low-density pattern of electromagnetic field values, and not—as conventionally done—at all positions across the mesh (which may be understood as the entire region of interest) resulting in a high-density pattern of electromagnetic field values. The sparse electromagnetic field values are determined according to the present invention to accelerate the acquisition process in the radar tomography. Further, particularly in case of reconstructing a final image of the object or region of interest showing the determined material properties, as proposed according to an embodiment of the present invention, the high-density pattern of material properties, or the material properties at all elements of the mesh, is derived directly from the sparse electromagnetic fields determined at some (i.e. the low number) of the mesh elements.

Conventional approaches for sampling signals or imaging follow the Shannon's theorem, which establishes that the sampling rate must be at least twice the maximum frequency present in the signal (also called Nyquist rate). This principle has been applied in many signal acquisition protocols used in consumer audio or image electronics, medical imaging devices, digital communications, etc. When the signal is bandlimited, as it used to be in the digital communications field, to convert the analog signals into the digital domain requires the usage of analog-to-digital converters (ADCs), sampling at or above the Nyquist rate, which implicitly imposes a dependency of such systems on the ADC capabilities. For other signals like images, the required sampling rate is not dictated by the Shannon's theorem but by the desired temporal or spatial resolution. However, it is common to such systems to use antialiasing low-pass filters to bandlimit the signal before sampling, and then the Nyquist rate plays also here an important role.

The compressive sensing paradigm, as described, for instance, in E. Candes, J. Romberg, and T. Tao, "Robust uncertainty principles: Exact signal reconstruction from highly incomplete frequency information," IEEE Transactions on Information Theory, vol. 52, pp. 489-509, 2006 or D. Donoho, "Compressed sensing," IEEE Transactions on Information Theory, vol. 52, pp. 1289-1306, 2006, goes against that common wisdom in data acquisition, by asserting that it is possible to recover certain signals and images from far fewer samples or measurements than those required from the traditional methods. In contrast to the conventional sampling theorem, which assumes that the amount of information in a signal is proportional to its frequency content, compressive sensing proposes a new sampling paradigm in which the information content of the signal is determined by its sparsity level or by its degree of freedom. From this point of view, the signal of interest does not need to be sampled at Nyquist rate, but at its information rate, which—in most of the cases—is much less than its bandwidth.

Briefly summarized, the compressive sensing paradigm establishes that if a signal or image is sparse enough in some known domain, it can be reconstructed from a very few number of samples (much less than what Nyquist specifies), as far as the acquisition process can be randomized in some sense. Hence, the present invention proposes to reduce the data acquisition time of a radar tomography apparatus by applying compressive sensing. Consequently, the compressive sensing technology is applied in the processing of the acquired sparse pattern of the electromagnetic field values to construct the material properties at a high number or even all the mesh elements leading to the desired advantages over the known radar tomography devices and methods, in particular leading to the desired reduction in processing time. Further, an increase in the resolution of an image that can be reconstructed from the obtained material properties can be obtained if desired.

To apply the compressive sensing technique to radar tomography it is necessary first of all to find a measurements domain where the image formed by the material properties of the object has a sparse representation. One characteristic of the radar tomography images that is being considered here is that they are piecewise constant, since the gradient of the image or material properties is sparse in nature. Therefore, one possibility is to use the total variation technique, as proposed according to an embodiment, for recovering the image from a small number of electromagnetic field measurements, but other sparse representations are also possible.

The second condition to successfully apply compressive sensing is that the way the measurements are done (i.e. a measurement matrix) has to be incoherent with the representation basis being used (i.e. a representation matrix). The coherence measures the largest correlation between any two elements in these two matrices. One way to ensure this condition is to select a (pseudo-)random matrix as a measurement matrix, i.e. to randomize the acquisition process. Other measurement matrices are also possible, and depending upon the object to be subjected to the radar tomography a customized measurement matrix could have better incoherence than a randomly selected one. However, a random one is generic and object independent.

The solution proposed according to the present invention is to reduce the data acquisition and processing time by determining fewer electromagnetic field values in the forward solver than in a standard process, and then process the values by applying compressive sensing using the sparse representation of the material properties of the object under study (like, for example, total variation).

The application of compressed sensing proposed according to the present invention varies from current state of the art methods where it is applied to "Computed Tomography (CT)". There, a linear relation between the measurements and the image is usually assumed as, for instance, disclosed in H. Yu and G. Wang, "Compressed Sensing based interior tomography", Physics in Medicine and Biology, October 2009. Assuming a linear relation between the electromagnetic fields and the image in radar tomography would be the straightforward solution for radar tomography; however, it has been found that the results will not be satisfactory unless prior information is known. Compressive sensing can be also employed to reduce the acquisition time in radar tomography as was done in "Photo-Acoustic Tomography (PAT)" as, for instance, described in Jean Provost and Frederic Lesage "The Application of Compressed Sensing for Photo-Acoustic Tomography", IEEE Transactions on Medical Imaging, April 2009. This, however, will reduce the acquisition time but it only covers a limited view of the object.

An element of the present invention is to reconstruct the image by formulating the compressive sensing principle to suit the non-linear inverse scattering problem in radar tomography. The non-linear inverse scattering problem assumes a non-linear relation between the electromagnetic fields and the image (material properties). A model modeling such a relation is also used in breast cancer detection, as, for example, described in A. E. Bulyshev et al. "Three-dimensional vector microwave tomography: theory and computational experiments", Inverse Problems, August 2004, because it results in high quality images. However, the use of such a model makes the computations time demanding since, when the material properties of the whole object needs to be determined, the number of mesh elements where the relation should be determined will be very large. Hence, according to the present invention the principle of compressive sensing is applied, e.g. for breast cancer detection, to reduce the computation time.

BRIEF DESCRIPTION OF THE DRAWINGS

These and other aspects of the present invention will be apparent from and explained in more detail below with reference to the embodiments described hereinafter. In the following drawings FIG. 1 shows two embodiments of a general layout of a radar tomography apparatus, FIG. 2 shows a dense mesh and a coarse mesh used for data acquisition in a radar tomography apparatus.

DETAILED DESCRIPTION OF THE INVENTION

Figure 3:
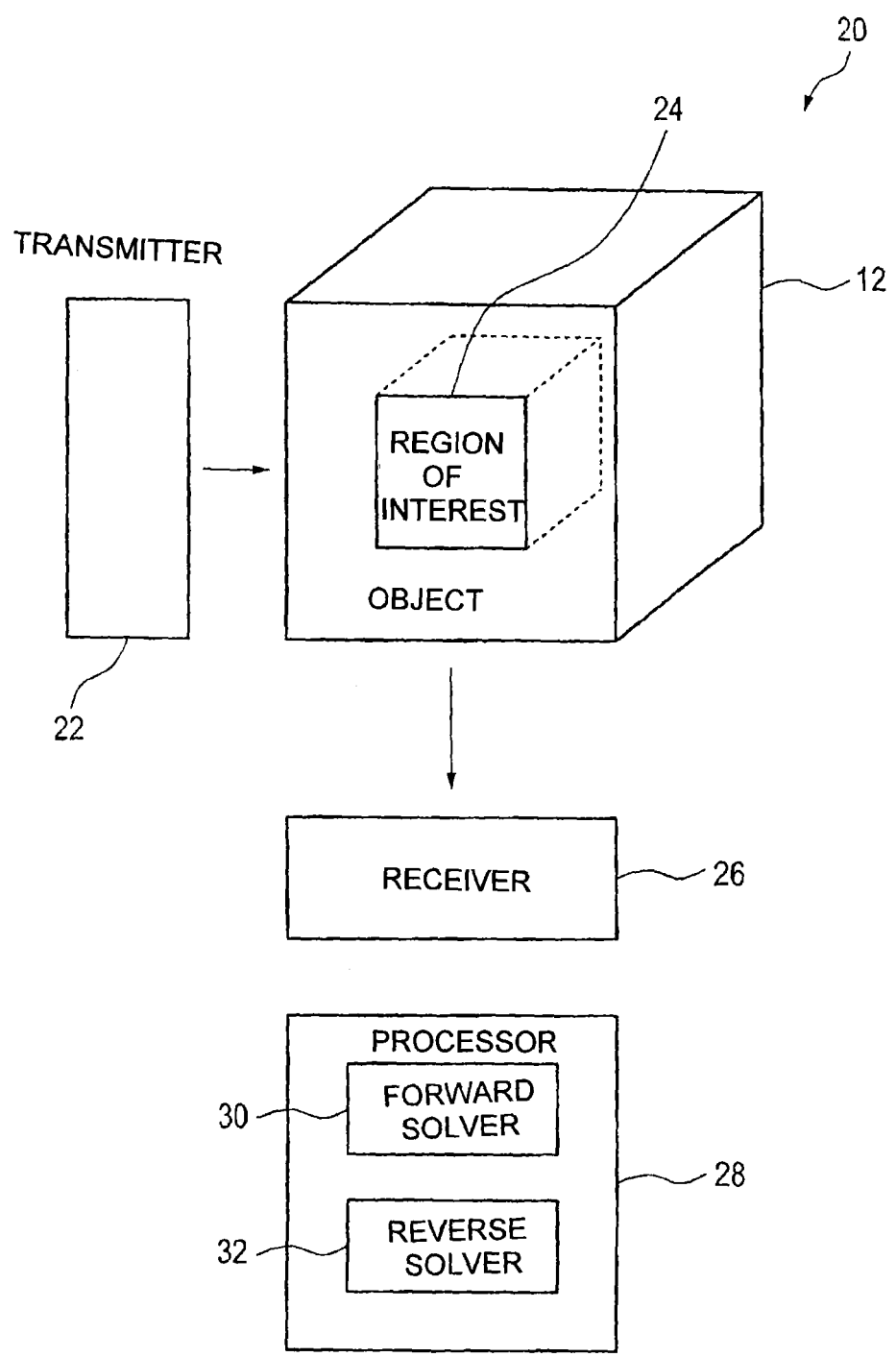
FIG. 3 shows a schematic block diagram of an embodiment of a radar tomography apparatus according to the present invention.

Radar tomography is a well known technique to construct the material properties of objects. It can be applied in vast areas like biomedicine to study the properties of tissues and determine whether they are malignant or not. It has been applied for example to breast and lung cancer imaging. It has also been applied to detect clots in brains and to study the cardiac activities.

An embodiment showing the general layout of a radar tomography apparatus 10 is shown in FIG. 1. An object 12, e.g. a patient or a probe of tissue, is placed within a volume V that has the form of a cuboid (FIG. 1A) or a cylinder (FIG. 1B) for example (other formats are possible). On the surface S of this volume, an array of transceivers 14 is placed in a way to surround the object 12, wherein the transceivers can also be replaced by separate transmitters and receivers, which may be arranged at different positions and may be different in number.

The objective of radar tomography is to compute the material properties of the object. Material properties are particularly the dielectric constant $\in(r)$, the conductivity $\sigma(r)$, and the magnetic permeability $\mu(r)$ at a specific location $r=(x, y, z) \in V$. It is important to note that in some radar tomography scenarios, some of these variables might be constant or known and need not to be evaluated.

In radar tomography, the first step is to compute the complex electromagnetic fields, i.e. E(r) and H(r), at every point within the volume V and for every transmitter. This problem is called the forward solver. Since there is infinite number of points in V, the domain is subdivided into a mesh. Example subdivisions are shown in FIG. 2 by taking a 2D slice of the cubic volume V shown in FIG. 1A for simplicity. In FIG. 2, the volume V is subdivided into small square regions which in 3D will be equivalent to voxels (small cubes), wherein FIG. 2A shows a dense mesh 16 having a high number of voxels compared to the mesh shown in FIG. 2B showing a coarse mesh 18. The mesh can also have other forms like a triangular mesh for example. Whatever the mesh form is, the importance is to compute the complex electromagnetic fields at each of these elements. Therefore, the denser the mesh is the more accurate is the computation of the fields. However, the computational cost will also increase dramatically. In the meshes shown in FIGS. 2A and 2B, the entire domain represents the region of interest where the complex fields should be computed, but one can also limit the region to cover the object with the unknown material properties alone or with some of its surrounding region.

An embodiment of a radar tomography apparatus 20 according to the present invention is schematically shown in FIG. 3. The radar tomography apparatus 20 is provided for determining one or more material properties of an object 12 at a first number of positions distributed within a region of interest of said object 12. For this purpose, it comprises one or more transmitters 22 that transmit radiation, in particular microwave radiation (generally up to 10 GHz for medical applications, but can be up to 300 GHz for other applications, e.g. security applications like concealed weapon or explosives detection), in the direction of the region of interest 24 of the object 12, a plurality of receivers 26 that receive radiation reflected from or transmitted through the region of interest 24 of the object 12, and a processor 28 that processes the received radiation. Said processor 28 includes a forward solver 30 that determines electromagnetic field values at a second number of positions distributed in the region of interest 24 from the received radiation, wherein said second number is substantially lower than said first number, and an inverse solver 32 that determines one or more material properties of the object 12 at the first number of positions in the region of interest 24 from the electromagnetic field values determined at said second number of positions in the region of interest 24 by applying compressive sensing. The essential steps performed by said apparatus will be explained in detail below.

Before showing how to determine the electromagnetic fields in the forward solver 30, a model of the field propagation generated in an embodiment, which model is based on Maxwell's equation of electromagnetic waves. One form of the Maxwell's equation is used herein to explain an essential idea of the present invention is the time-harmonic model which is written in the form:

$$\nabla \times H(r) = i\omega\varepsilon(r) + J(r) \quad \nabla \times E(r) = -i\omega\mu(r) \quad (1)$$
$$\nabla \cdot (\mu(r) \cdot H(r)) = 0 \quad \nabla \cdot (\varepsilon(r) \cdot E(r)) = \rho(r)$$

The variable $\omega$ is the angular frequency, E(r) is the vector electric field, H(r) is the vector magnetic field, J(r) the current density, $\rho(r)$ is the electric charge density and the constant $i = \sqrt{-1}$. The complex fields E(r) and H(r) are computed in the forward solver by solving variations of the above equations at each of the mesh elements.

Depending on the problems at hand and the assumptions made, variations of equation (1) are solved in the state of the art which might lead to different types of algorithms been used for the forward solver. In biomedical applications for example, the permeability is assumed to be constant since biological tissues are not magnetic and only the dielectric constant and conductivity are of interest. In addition, electric charge density $\rho(r)$ is assumed to be null. Although such assumptions might simplify the complexity of the problem to be solved, still a vast number of variables need to be determined depending on the density of the mesh as explained above with reference to FIG. 2.

In the forward solver 30, methods like Finite Difference Time Domain (FDTD), Finite Elements (FE), Fast Fourier Transforms (FFT) or even iterative techniques like Newton based schemes are used to compute the electromagnetic fields, as also described in the above cited documents. Once the fields are computed, they are used to estimate the material properties using an inverse solver 32. Like the forward solver 30, there are many proposed algorithms in the state of the art to compute the inverse solution. All of these algorithms proceed by formulating a cost function C after discretizing the equations from (1) as $$C(\varepsilon, \sigma, \mu) = \sum_{l,m} \|S_{l,k}^{th} - S_{l,k}^{ex}\|_2 + R(\varepsilon, \sigma, \mu) \quad (2)$$

The variable S is a function of the complex electromagnetic fields E(r) and H(r), the subscript l is the transmitter number, the subscript m is the receiver number, the superscripts th and ex denote the theoretical and the measured values of the function respectively and the operator $\|\cdot\|_2$ denotes the L2 norm. In its simplest form, the function S can be the difference between the measured and theoretical values of the electric fields themselves and the term inside the summation will be in this case $\|E_{l,k}^{th} - E_{l,k}^{ex}\|_2 + \|H_{l,k}^{th} - H_{l,k}^{ex}\|_2$. In a more general case, the function S can take the model of the antenna used into account or some other factors. The right addend in equation (2) is the regularization term. It is applied in the cost function since the inverse problem is ill-posed. This occurs in practice since the measured values of the complex fields are noisy and make the computations unstable. In the state of the art, the Tikhonov method is mostly used (see for example the above cited paper of A. E. Bulyshev et al.). To solve this equation, Newton based iterative methods like conjugate gradient and Gauss Newton are applied. Like the forward solver 30, the denser is the mesh the more complex will the computation of the solution be in the inverse solver 32.

The present invention proposes to apply the concept of compressive sensing (CS) to accelerate the computational complexity in radar tomography. Compressed or compressive sensing (CS) is the art of reconstructing a signal from some random measurements that directly condense the original signal into a compressed representation. The measurements acquired are condensed in the sense that they are very low in number which makes further compression not necessary. CS differs from the traditional data acquisition schemes since it does not follow the "sample first—then compress" framework. The bottleneck here lies in the methodology that should be used to reconstruct the original signal from the measurements. To integrate CS in radar tomography, it should be taken into account how the measurements for CS reconstruction are acquired, which part is accomplished before the forward solver that computes the complex electromagnetic fields, and how the dense material properties are reconstructed from the sparse measurements that are needed to obtain the final result, e.g. a image or a data set of the desired material properties. These two points will be described in more detail below.

In the following, $\Phi$ designates the sub-sampling matrix, M designates the mesh matrix, m is the vector format of M taken by padding its columns, Y is the matrix containing some sub-elements of M and y is the vector format of Y taken by padding its columns. The dimensions of M and respectively m depends on the density of the mesh and the dimension of the problem. Reference is again made to the previously mentioned example about the cubic region of dimensions 15×15× 15 cm³ which was divided into 100×100×100 voxels. The dimensions of M in this case will be also 100×100×100 in 3D while it is only 100×100 for any 2D slice. These numbers get larger with additional transmitted signals and with multi-frequency approaches.

An essential first step is to design a suitable sub-sampling matrix $\Phi$ that can define the measurements. The sub-sampling matrix should satisfy the properties of compressive sensing. To do that, it is necessary to choose a sub-sampling matrix that makes the sampling process acts like incoherent aliasing interference. The incoherent aliasing interference property can be satisfied if the sub-sampling matrix satisfies the restricted isometry property (RIP), as also described in the above cited document generally describing compressive sensing. Any sub-sampling matrix that satisfies the RIP or ensures that the sub-sampling process acts like incoherent aliasing interference can be used according to the present invention. The simplest form of a sub-sampling matrix that ensures this property is a pseudo-random sampling matrix. Irrespective of the matrix $\Phi$ chosen, the sampling process will result in an irregular sampling pattern from M. The resulting Y and hence y should follow the mapping defined by $$\Phi \cdot m = y \quad (3)$$

Figure 4:
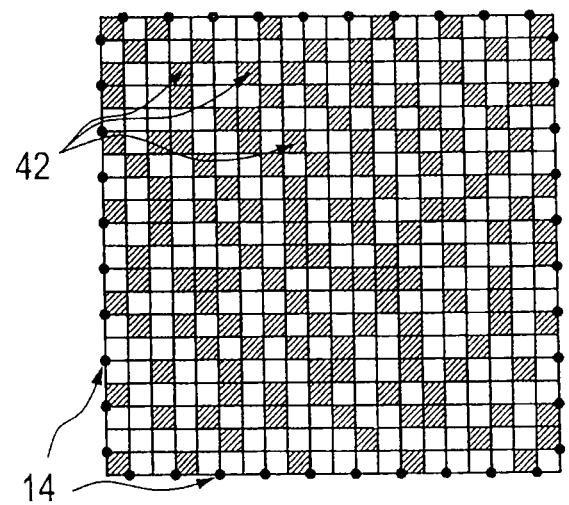
FIG. 4 shows an embodiment of a sparse mesh in 2D domain as used in an embodiment of the present invention.
Figure 5:
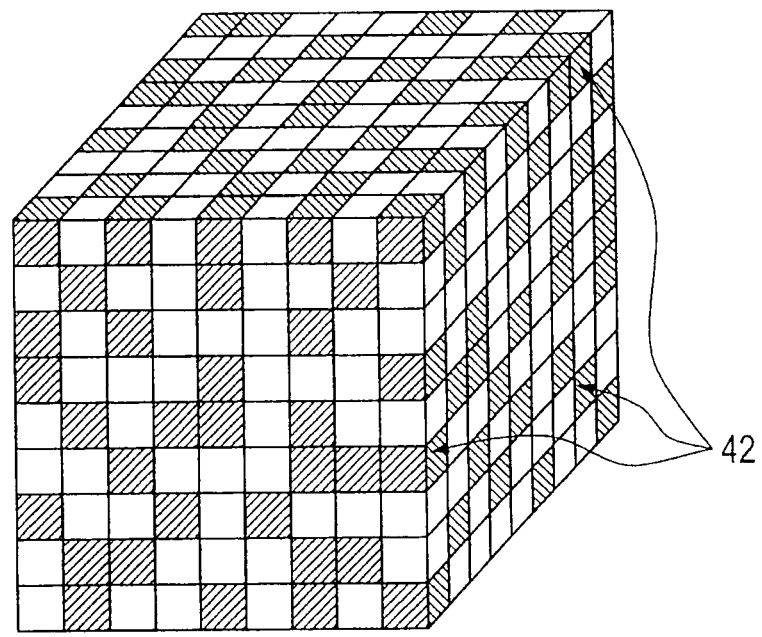
FIG. 5 shows an embodiment of a sparse mesh in 3D domain as used in an embodiment of the present invention.

Doing that, y will have a total number of K elements while the total number of elements in m is L where K<<<<L. To visualize that for the present invention and the problem to be solved, an example is shown in FIG. 4 for the 2D case showing a sparse 2D mesh 40 and in FIG. 5 for the 3D case showing a sparse 3D mesh. The elements of the vector y in both cases are highlighted in grey. These highlighted elements represent the second (low) number of positions, which are distributed over the whole volume V (representing the region of interest) and at which the electromagnetic field values are determined. These elements are chosen according to the sub-sampling matrix $\Phi$. As can be seen, said second number of (grey) elements is substantially lower than the first number of all elements of the mesh.

Once y is determined, the forward solver 30 in radar tomography is invoked using y to compute the irregular sparse complex electromagnetic fields $E_i(r)$ and/or $H_i(r)$ at each of the elements of y. The subscript i is added here to differentiate the regular sparse fields that are usually computed in the state of the art and the sparse fields that are computed according to the present invention. The complex fields are preferably computed by applying methods like FDTD, FE, FFT or Newton based iterative schemes as done in the state of the art. Such forward solvers are generally known in the art (e.g. from the above cited references) and will thus not be described in more detail here.

Since the number of elements of y and hence Y is much less than m, the computations of the forward solver will be faster since the complex electromagnetic fields should be computed at less points in V. The (e.g. irregular) sparse electromagnetic fields $E_i(r)$ and $H_i(r)$ computed with the forward solver represent the CS measurements that will be used to estimate the image of the material properties using the inverse solver which will be explained next.

Now that the measurements $E_i(r)$ and $H_i(r)$ are computed according to the sub-sampling matrix $\Phi$ and the forward solver, the dense material properties are recovered next from $E_i(r)$ and $H_i(r)$. The idea is to find a sparsifying transformation where the material properties $\in(r)$, $\sigma(r)$, and $\mu(r)$ are sparse with respect to the complex electromagnetic fields and at which the reconstruction algorithm can be designed. This sparsifying transformation should also take the properties of the material properties into account. It is well known in that the material properties are piece-wise smooth entities. In other words, the distribution of each of the material properties varies smoothly except at the edges.

In one preferred embodiment, the total variation (TV) operator is used since it ensures that material properties are smooth except at the edges. The total variation resumes in computing the gradient of the material properties in each dimension. It can be written for the dielectric constant $\in(r)$ as $$TV(\varepsilon(r)) = \sum_V |\nabla \varepsilon(r)| \quad (4)$$

The operator $|\cdot|$ is the absolute value. Similar equations can be formed for $\sigma(r)$ and $\mu(r)$. As alternative embodiment to the total variation, it is also possible to select a basis for each of the material properties using the Fourier or the wavelet basis and assuming that such basis is sparse and preserve the properties of the materials being piecewise smooth. Moreover, it is possible to use a Fourier or a wavelet basis for the material properties in combination with the total variation. However, this solution leads to a higher complexity than taking the total variation alone, which represents the preferred embodiment of the invention. Having this in mind, the cost function of the preferred embodiment that has to be minimized to give the estimate of the dense material properties is given by $$\operatorname*{argmin}_{\varepsilon,\sigma,\mu} [\|TV(\varepsilon(r), \sigma(r), \mu(r))\|_p] \text{ such that } \sum_{l,m} \|S_{l,k}^{th} - S_{l,k}^{ex}\|_2 = 0 \quad (5)$$

The operator $\|\cdot\|_p$ is the Lp norm. To obtain the material parameters using the compressive sensing formulation, any L1-norm optimization algorithm is preferably, i.e. p=1. Example algorithms suitable for the above equation are basis pursuit, non-linear conjugate gradient, as described in the above cited documents generally describing compressive sensing. Other type of algorithms like the L0-norm optimization schemes or any construction algorithm suitable for compressive sensing may, however, also be used.

It should be understood that the cost function in equation (5) represent a preferred embodiment in the general case where all of the parameters $\in(r)$, $\sigma(r)$, and $\mu(r)$ require to be estimated. In some applications like in biomedicine, only $\in(r)$ and $\sigma(r)$ need to be computed. In such cases, the cost function (5) can be modified accordingly to compute $\in(r)$ and $\sigma(r)$ only since $\mu(r)$ is assumed to be constant over V. It is also possible to add some other terms to equation (5) if a combination of a sparse basis like FFT or wavelet is to be considered with total variation or the sparse basis alone.

Figure 6:
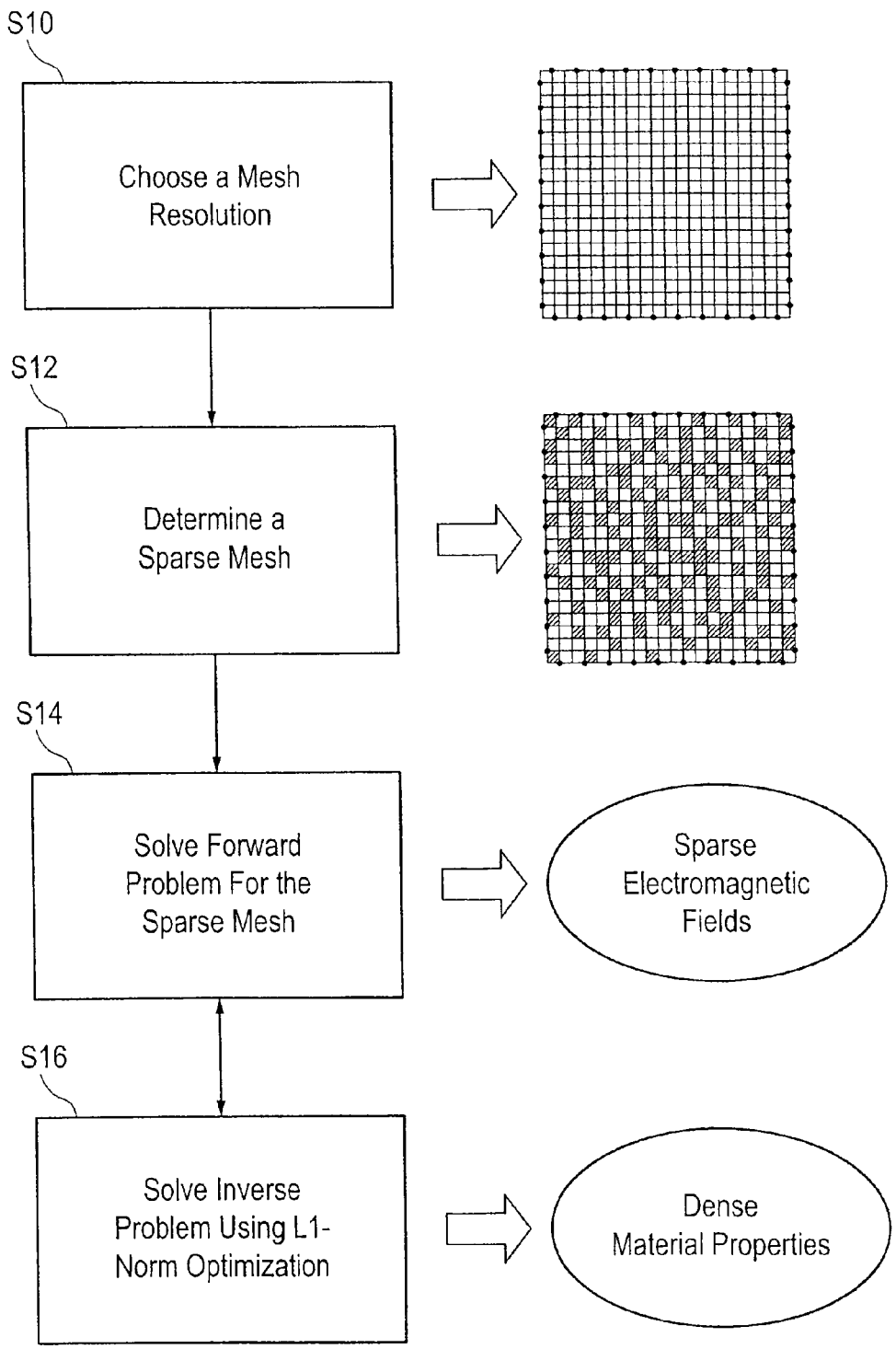
FIG. 6 shows a flow chart illustrating an embodiment of the radar tomography method according to the present invention.

A flowchart describing a preferred embodiment of the present invention is shown in FIG. 6. It shows all the steps necessary to perform compressed radar tomography in an embodiment. To summarize the procedure, a mesh resolution is specified in step S10 for the volume V where the computations of the complex electromagnetic fields need to be determined. Then, in step S12 a sparse mesh, e.g. an irregular, random or quasi-random mesh, is chosen as described above. In step S14 the forward solver computes the complex fields using the sparse mesh at the second (low) number of positions. Having obtained the sparse complex electromagnetic field values, the algorithm proceeds to step S16 with the inverse solver to estimate the values of the materials properties at the first (high) number of positions.

It shall be remarked that a double sided arrow was placed before this last step. This actually depends on the algorithm used to optimize equation (5). Some algorithms might require a repeated forward solution in each iteration of the inverse solver while others require the forward solution only once.

Figure 7:
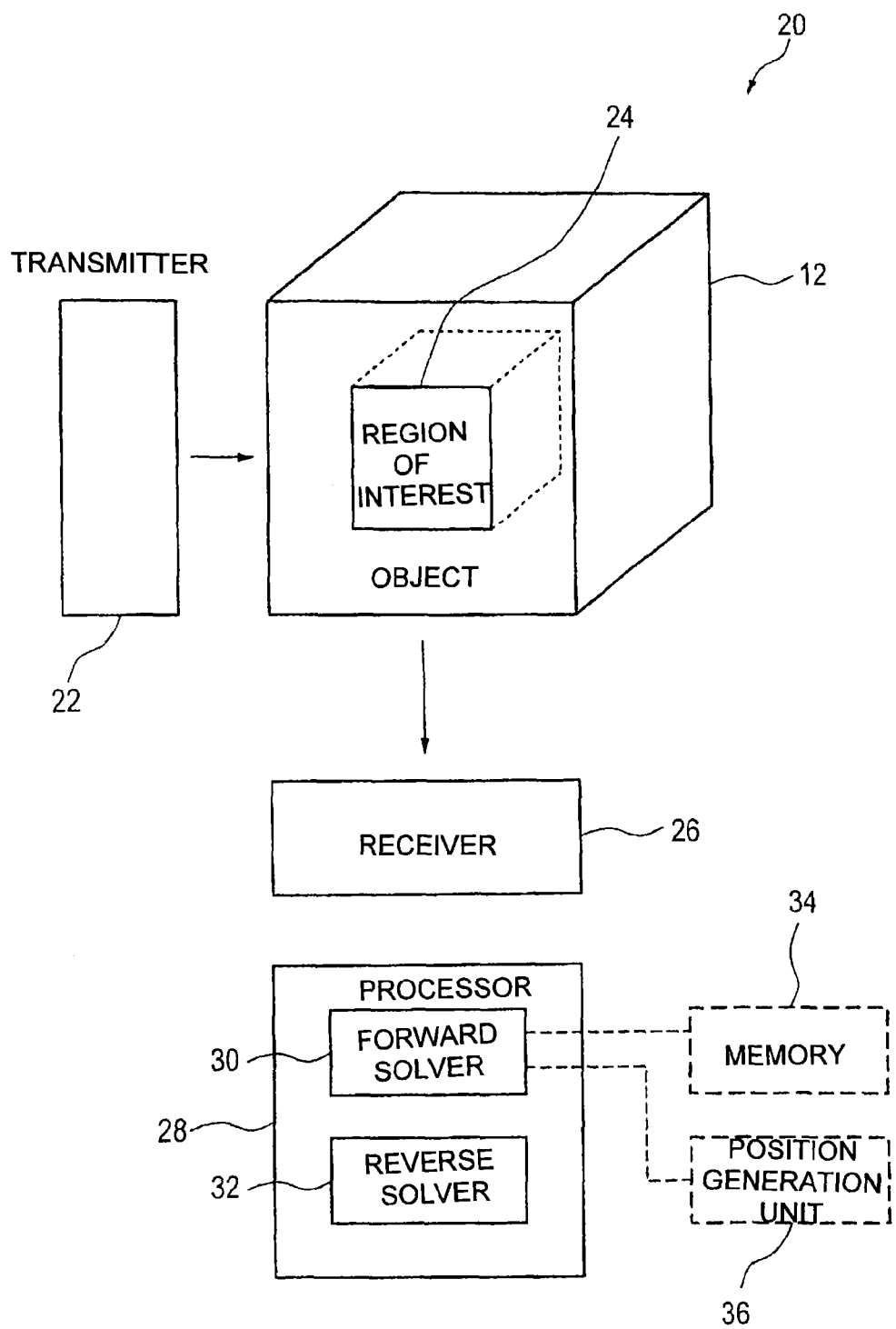
FIG. 7 shows another embodiment of a radar tomography apparatus according to the present invention.

FIG. 7 schematically shows another embodiment of a radar tomography apparatus according to the present invention. In addition to the elements shown in the embodiment depicted in FIG. 3, a memory 34 is provided that stores one or more lists of positions, at which electromagnetic field values shall be determined by said forward solver 30. The forward solver 30 is accordingly configured to select the second number of distributed positions at which said electromagnetic field values are determined from one or more lists stored in a memory 34.

Alternatively or in addition, a position-generation unit 36 is provided that determines the positions at which electromagnetic field values shall be determined by use of a predetermined function or sampling distribution. For instance, a uniform Bernoulli or Gaussian distribution is used for this purpose.

The positions may thus be generated on the fly by use of a generator, e.g. a processor, for calculating the positions. For instance, a pseudo-random number generator can be applied for implementing said embodiment.

Various embodiments for the inverse solver 32 exist. Preferably, the inverse solver applies a L1-norm minimization algorithm to said electromagnetic field values determined at said second number of positions and the region of interest to determine the material properties. The L1-norm is generally known, and the L1-norm problem (also called least absolute deviations (LAD), least absolute errors (LAE), least absolute value (LAV)) is a mathematical optimization technique similar to the popular least squares technique (L2-norm) that attempts to find a function which closely approximates a set of data. In the simple case of a set of (x, y) data the approximation function is a simple "trend line" in 2D Cartesian coordinates. The proposed method thus minimizes the sum of absolute errors (SAE) or sum of "residuals" between points generated by the function and corresponding points in the data.

Other norms can, however, also be used according to the present invention. Further, in an embodiment a total variation algorithm is applied by the inverse solver 32.

Also for the forward solver 30 various embodiments exist. For instance, in one embodiment the forward solver 30 is configured to determine electromagnetic field values at a second number of positions irregularly distributed in a region of interest. In this context "irregular" shall be understood such that the positions at which electromagnetic field values are determined are not located at equal distances in at least one direction (preferably in both or all directions) of the mesh (e.g. a Cartesian grid). By such an irregular distribution a certain degree of randomness is achieved as preferred for applying the compressive sensing technique.

According to a further embodiment, the forward solver 30 is configured to determine electromagnetic field values in a second number of positions randomly or quasi-randomly distributed in the region of interest. This is, for instance, done by applying methods like FDTD, FE, FFT or Newton based iterative schemes as done in the state of the art on the irregularly distributed positions at which electromagnetic field values are determined.

In still another embodiment the forward solver 30 is configured to determine electromagnetic field values at a second number of positions, which is by a factor in the range from 10% to 90%, in particular in the range from 25% to 75%, lower than the first number. Hence, compared to conventional radar tomography methods, according to this embodiment electromagnetic field values are determined at substantially fewer positions. For instance, electromagnetic field values may be acquired at approximately 50% of the total number (first number) of available positions, nevertheless resulting in a fairly good result after applying compressive sensing to construct the material properties at all the mesh elements using the inverse solver in 32. Generally, there is a trade-off between the number of positions (i.e. the reduction of data acquisition processing time) and the desired quality of the results of the data acquisition and data processing.

The invention has been illustrated and described in detail in the drawings and foregoing description, but such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A radar tomography apparatus for determining one or more material properties of an object at a first number of positions distributed within a region of interest of said object, said apparatus comprising:

one or more transmitters that transmit radiation in the direction of the region of interest of the object, a plurality of receivers that receive radiation reflected from or transmitted through the region of interest of the object, a processor that processes the received radiation, said processor including a forward solver that determines electromagnetic field values at a second number of positions distributed in the region of interest from the received radiation, wherein said second number is substantially lower than said first number, and an inverse solver that determines one or more material properties of the object at the first number of positions in the region of interest from the electromagnetic field values determined at said second number of positions in the region of interest by applying compressive sensing.

2. The radar tomography apparatus as claimed in claim 1, wherein said inverse solver is configured to apply a l1-norm minimization algorithm to said electromagnetic field values determined at said second number of positions in the region of interest.

3. The radar tomography apparatus as claimed in claim 1, wherein said inverse solver is configured to apply a total variation algorithm to said electromagnetic field values determined at said second number of positions in the region of interest.

4. The radar tomography apparatus as claimed in claim 1, wherein said inverse solver is configured to determine the dielectric constant, the conductivity and/or the magnetic permeability of the object.

5. The radar tomography apparatus as claimed in claim 1, wherein said forward solver is configured to determine electromagnetic field values at a second number of positions irregularly distributed in the region of interest.

6. The radar tomography apparatus as claimed in claim 1, wherein said forward solver is configured to determine electromagnetic field values at a second number of positions randomly or quasi-randomly distributed in the region of interest.

7. The radar tomography apparatus as claimed in claim 1, further comprising a memory that stores one or more lists of positions, at which electromagnetic field values shall be determined, wherein said forward solver is configured to select the second number of distributed positions from said one or more lists.

8. The radar tomography apparatus as claimed in claim 1, further comprising position generation means that determines the positions, at which electromagnetic field values shall be determined by use of a predetermined function or sampling distribution, in particular a uniform Bernoulli or Gaussian distribution.

9. The radar tomography apparatus as claimed in claim 1, wherein said receivers and said transmitters are implemented as a plurality of transceivers.

10. The radar tomography apparatus as claimed in claim 1, wherein said forward solver is configured to determine electromagnetic field values at second number of positions, which is by a factor in the range from 10% to 90%, in particular in the range from 25% to 75%, lower than the first number.

11. A radar tomography method for determining one or more material properties of an object at a first number of positions distributed within a region of interest of said object, said method comprising:

transmitting radiation in the direction of the region of interest of the object, receiving radiation reflected from or transmitted through the region of interest of the object, processing the received radiation by determining electromagnetic field values at a second number of positions distributed in the region of interest from the received radiation, wherein said second number is substantially lower than said first number, and determining one or more material properties of the object at the first number of positions in the region of interest from the electromagnetic field values determined at said second number of positions in the region of interest by applying compressive sensing.

12. A non-transitory computer readable medium having instructions stored thereon which, when carried out on a computer, cause the computer to perform the method as claimed in claim 11.

13. A radar tomography apparatus for determining one or more material properties of an object at a first number of positions distributed within a region of interest of said object, said apparatus comprising:

one or more transmission means for transmitting radiation in the direction of the region of interest of the object, a plurality of receiving means for receiving radiation reflected from or transmitted through the region of interest of the object, a processing means for processing the received radiation, said processing means including a forward solving means for determining electromagnetic field values at a second number of positions distributed in the region of interest from the received radiation, wherein said second number is substantially lower than said first number, and an inverse solving means for determining one or more material properties of the object at the first number of positions in the region of interest from the electromagnetic field values determined at said second number of positions in the region of interest by applying compressive sensing.

* * * * *